United States Patent [19]

Rosenfeld

[11] Patent Number: 5,051,091
[45] Date of Patent: Sep. 24, 1991

[54] SIMPLIFIED DENTAL IMPLANT OPERATION

[76] Inventor: Philip J. Rosenfeld, 7 Edgemont Rd., Glen Rock, N.J. 07452

[21] Appl. No.: 599,028

[22] Filed: Oct. 17, 1990

[51] Int. Cl.⁵ ............................ A61C 8/00; A61C 5/00
[52] U.S. Cl. .................................. 433/201.1; 433/173; 433/175; 433/215
[58] Field of Search ............... 433/215, 172, 173, 174, 433/201.1

[56] References Cited

U.S. PATENT DOCUMENTS 4,713,004 12/1987 Linkow et al. ...................... 433/174
4,713,006 12/1987 Hakamatsuka et al. ........... 433/201.1

FOREIGN PATENT DOCUMENTS 9151951 2/1983 Japan .................................. 433/201.1

Primary Examiner—John J. Wilson
Assistant Examiner—Cindy A. Cherichetti
Attorney, Agent, or Firm—Richard C. Litman

[57] ABSTRACT

A simplified operation for setting a dental implant into bone following tooth extraction uses the cavity left by the extraction rather than drilling. To hold the implant in the proper position in the tooth cavity, it is braced with resorbant material. The implant can be surrounded by resorbant material in various ways: it may be emplaced between two blocks of resorbant material, the blocks sewn together, and the combination inserted into the cavity; or resorbant material may be cut into a strip and the implant rolled up in the strip prior to insertion. Additional resorbant material can be inserted to adjust the position of the implant. With the implant properly aligned, the gums flaps are sutured over the resorbant material and implant. In time, bone will grow around the implant and firmly fix it into the bony structure. A dowel or abutment head may then be mounted to the implant for attaching a prosthetic tooth, bridge, or the like.

7 Claims, 1 Drawing Sheet

SIMPLIFIED DENTAL IMPLANT OPERATION

FIELD OF THE INVENTION

The present invention relates to dental operations for fixing biointegrated implants into bone underlying the gums following a tooth extraction.

DESCRIPTION OF THE PRIOR ART

The usual procedure for setting a tooth implant after tooth extraction involves two operations.

The first operation is to extract the diseased tooth, insert resorbant material such as gelfoam or collagen into the cavity, and suture the gums closed.

(Resorbant material may be defined to be any body-absorbable substance used to form a blood clot. It is commonly used in surgery to fill body voids. Resorbant material is so called because it is resorbed, or absorbed, by the body over a period of time.

Gelfoam is a sterile dehydrated gelatinous substance having an open foam structure. Its consistency is like that of Styrofoam, but more flexible. It is absorbed by the body in about three months following insertion during surgery. When initially placed in the body it swells. Gelfoam has been widely used in surgery of all types for many years. The term "gelfoam" is not a trademark. The primary supplier of gelfoam to the medical industry is the Upjohn Company.

A new resorbant material product, collagen, is coming onto the market.)

The resorbant material in the tooth socket becomes soaked with blood, and a clot forms. This clot is gradually replaced by bone through the natural healing process of ossification: the surrounding bone grows into the clot, and the cavity in the bone is filled with new bone.

Several months are allowed for the patient's recuperation and new bone formation. The second operation is performed only after healing from the first operation is verified. X-rays or other imaging techniques are used to check that the bone which has replaced the resorbant material is formed properly, and is of sufficient thickness, width, and density. If it is, the second operation proceeds.

In the second operation, the gum is reopened and a hole is drilled into the newly-formed bony tissue for the insertion of an implant. This drilling must be done slowly, with a low-speed, high-torque hand drill, to prevent burning the bone along the sides of the drilled hole. If the bone is damaged, it will not grow onto the implant.

A surgical template (i.e., jig or fixture) may be used to align the drill bit. The template is made from a diagnostic cast of the area. The template insures that a hole is not drilled at the wrong place or angle, which would result in an uncentered implant hole, or damage to the bone or to adjacent teeth.

The implants are about 4 millimeters in diameter and 8 to 15 millimeters long. The hole is drilled a millimeter or two longer than the implant, because the bone surface will erode that much after the surgery.

The implant is made of a strong bio-compatible metal such as titanium. The implant surface is coated with an artificial bone substance, such as hydroxylapatite. This encourages bony growth onto the surface of the implant, for bio-mechanical locking of the implant to the bone. The implant may also have texture, or holes through its surface wherein bone may grow, to provide additional mechanical locking of the implant to the bone.

Implants of this type are sold by Calcitek, Inc., under the name "Integral". These have been shown to be effective, as reported in *JADA*, vol. 121, pps. 138-144, July 1990.

Other sorts of implants than the Integral implant can be used in these operations, if they are designed to biomechanically lock to bone through bone growth. Types of such implants are numerous.

For example, an implant having a mesh structure to encourage locking by embedding bone growth is disclosed in U.S. Pat. No. 4,842,517 of Kawahara et al.

Following the insertion of the implant and suturing of the gums in the second operation, 8 to 12 weeks of recuperation are allowed for bone to grow into contact with the implant surface and into any holes or other indentations of the implant. Again, diagnostic imaging is used to check the bone growth and insure that the implant is firmly fixed to the underlying bone structure.

If the bone growth is good, a dowel or an "abutment head" is joined to the implant. The joint is usually made either by cementing, or by a threaded extension on the abutment head which screws into a mating threaded hole in the implant. The dowel or abutment head serves as a base for the prosthetic tooth. Dowels are made of gold/palladium alloy.

The dowel or abutment head protrudes through the gum and serves to anchor a prosthetic tooth to replace the extracted tooth (or, it may anchor some other mechanical structure such as a dental bridge).

These operations with biointegrated implants have been a standard procedure for several years.

A related procedure is that of Freeman, disclosed in U.S. Pat. No. 3,919,773. Freeman's technique is to extract the natural tooth, and then fill the void left by the tooth with a moldable polymerizable or thermosetting material which will harden in place. The material is coated with soluble powder of specific particle size prior to insertion; the powder promotes attachment to either bone or gums, depending on particle size. Freeman does not employ ossification to grow new bone; rather, the material fills the gap in the bone left by the tooth, and any bone growth is onto the surface of the thermosetting material. Freeman does not disclose the use of resorbant material.

Freeman teaches the use of an implant, but the implant is not in contact with bone. Rather, the implant is embedded into the thermosetting material which hardens around it to lock it into place. No ossification is involved, and there is no disclosure in the Freeman patent of bony growth onto the surface of an implant (as opposed to bony growth onto the surface of moldable material).

None of the above inventions and patents, taken either singly or in combination, is seen to describe the instant invention as claimed.

The standard operations outlined above require the patient to endure two operations, each with a recuperative period of some months: the initial extraction, and the drilling operation. (The dowel or abutment head emplacement constitutes a third operation, but this is minor, as only the gum is opened, the incision is shallow, and there is little trauma.) These operations involve considerable time, expense, and pain. It would be a boon to patients if another method would reduce the time, expense, and pain.

Accordingly, one object of the present invention is a simplified operation to set into bone underlying the gums an implant to serve as a base for a prosthetic tooth.

Another object is to set such an implant in only one operation including an extraction.

A further object is to reduce the time, pain, and expense endured by a patient needing prosthetic teeth.

A final object is an operation which requires no surgical drilling template.

These and other objects of the present invention will become readily apparent upon further review of the following specification and drawings.

SUMMARY OF THE INVENTION

The present invention is a simplified operation for setting an implant into bone underlying the gums following a tooth extraction.

The natural tooth is extracted, leaving a cavity extending into the bone. An implant is set into the cavity. (The cavity may be enlarged by drilling if necessary.) To hold the implant in the proper position, it is braced with resorbant material. The implant can be surrounded by resorbant material in various ways: it may be emplaced between two blocks of resorbant material, the blocks sewn together, and the combination inserted into the cavity; or resorbant material may be cut into a strip and the implant rolled up in the strip prior to insertion. Additional resorbant material can be inserted to adjust the position of the implant.

With the implant properly aligned, the gums are sutured over the resorbant material and implant. In time, bone will grow around the implant and firmly fix it into the bony structure.

A dowel or abutment head may be mounted to the implant for attaching a prosthetic tooth, bridge, or the like.

DETAILED DESCRIPTION OF THE PREFERRED EMBODIMENT

Figure 1:
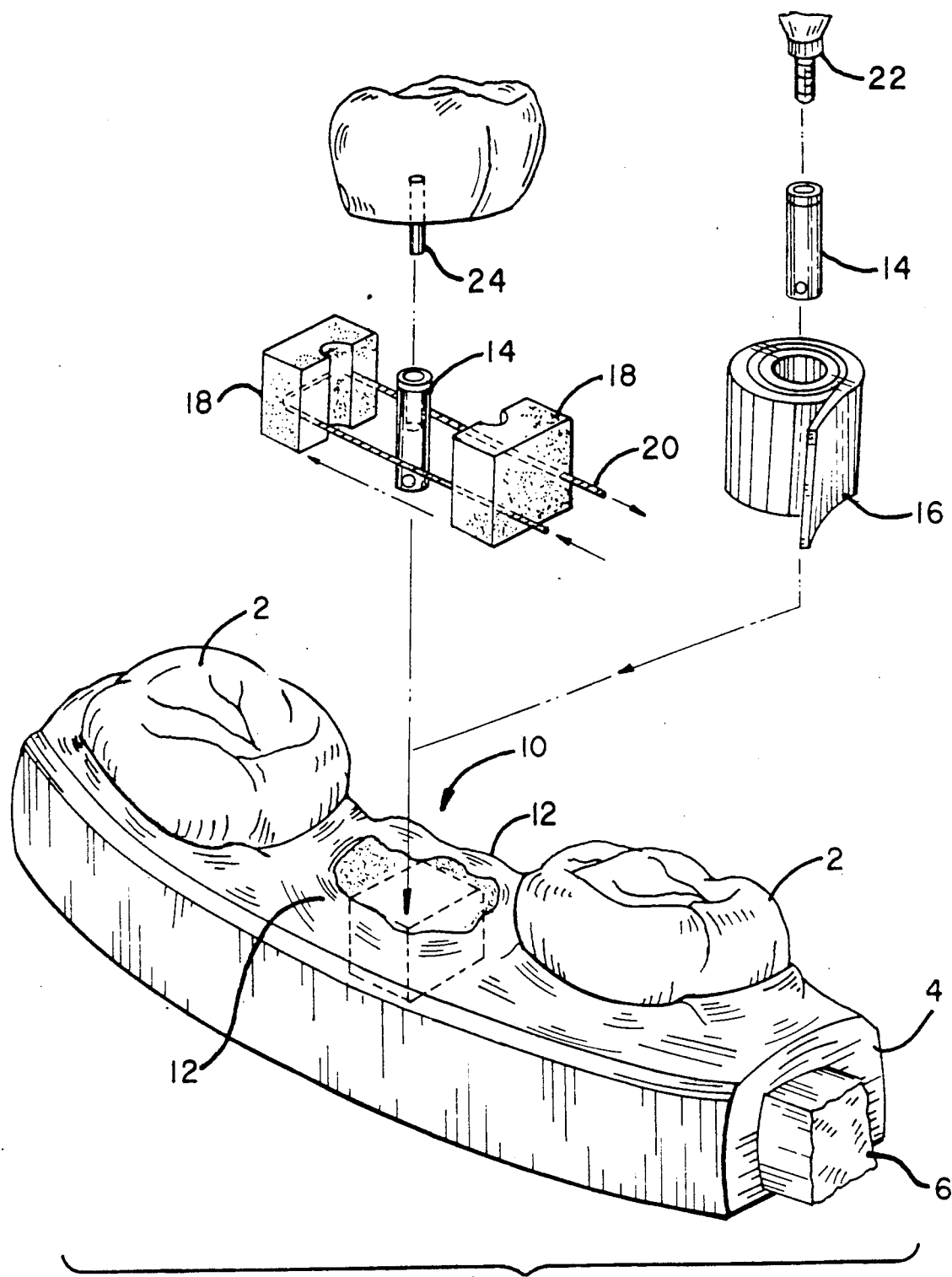
FIG. 1 shows gums and teeth and a cavity left by an extracted tooth. Exploded out of the cavity space are an implant, a rolled embodiment of resorbant material arranged to surround the implant, a block of resorbant material surrounding an implant, an abutment head, and a dowel.

Referring to FIG. 1, two teeth 2 are disposed on either side of a cavity 10 left by the extraction of a diseased tooth (the diseased tooth is not shown). Gum tissue 12 surrounds the cavity 10. The teeth 2 and cavity 10 both extend through the gum tissue 4 into the underlying bone 6 which supports the teeth.

In the procedure of the instant invention, the diseased tooth is extracted leaving the gums as shown in FIG. 1. Immediately after the extraction, an implant 14 is to be inserted into the cavity in such a way that, over time, the bone 6 will grow to attach to the implant 14.

To accomplish this, the implant 14 is surrounded with resorbant material prior to insertion into the cavity 10. The resorbant material will hold the implant in the proper position after the gums 12 are sutured together over the cavity 10, implant 14, and resorbant material.

Resorbant material in this specification means, any body-absorbable substance used to form a blood clot.

Two embodiments of the resorbant material surround are shown. The resorbant material may be cut into blocks 18 which are then sewn together around the implant 14 by dissolving-type suture threads 20. Or, a thin strip of resorbant material may be cut and rolled about an implant to form a more cylindrical shape 16.

Regardless of the mechanical method of surrounding the implant, the implant and resorbant material surround, assembled together, are inserted into the cavity as a unit. If necessary, the position of the implant can be adjusted by adding or removing resorbant material. Once the implant 14 is sufficiently deep into the cavity and angled correctly, the gums 12 are sutured closed, and the operation is complete. Blood will clot in the resorbant material. This clot will gradually be replaced with bone. Eventually, the implant will be surrounded by and embedded in bone, and firmly anchored.

If the extracted tooth is a lower anterior tooth (incisor), the cavity may be too narrow or to short to accept the implant and material surround. In this case the cavity may be enlarged by the use of an ordinary dental drill prior to insertion.

When the implant is firmly fixed and the bone healed, the gum 4 can be incised and the implant used as a mechanical attachment point. An abutment head 22 can be screwed into the threaded opening, or, a dowel 24 can be hammered into the opening in the top of the implant. These devices serve as intermediate supports to connect the implant to a prosthetic tooth, bridge, or the like.

In contrast to the prior art method of two separate surgical operations, the method of the present invention comprising one surgical operation is seen to involve approximately one half the expense, pain, and time involved in the prior art operations.

In addition, the instant invention does not require any drilling, and so does not require a specific type of low-speed, high-torque drill and special drill bits; nor is a surgical template for drilling required. Because no template is required, no diagnostic cast for fabricating the template is required, and no cast need be made.

If a tooth is removed for any reason, the present invention makes feasible the insertion of an implant for possible future use. Supposing that a person has a tooth extracted, but has no immediate need for an implant; with the prior art method, an implant would not be added due to the pain, trouble and expense. But the expense of inserting an implant by the present invention's method is small, so that the person may choose to have an implant inserted, merely on the chance that it might be needed in later years. If the implant is indeed later needed, the gum need only be incised to uncover the top of the implant.

Aseptic conditions are to be maintained during all of the above operations.

It is to be understood that the present invention is not limited to the sole embodiment described above, but encompasses any and all embodiments within the scope of the following claims.

I claim:

1. A method of embedding a dental implant including the steps of:

extracting a tooth to leave a cavity in the bone underlying the gums;

providing an implant;

forming resorbant material into at least one piece adapted to surround said implant and to hold said implant within said cavity in a proper position so that said implant may later serve as a mechanical support;

surrounding said implant with said piece;

inserting said implant and said piece into said cavity;
suturing the gums to enclose said implant and said piece within the gums;
waiting for said implant to affix to the bone underlying the gums by ossification and for the gums to heal; whereby
said implant upon affixing may serve to mechanically support a dental prosthesis or device.

2. A method of embedding a dental implant including the steps of:
extracting a tooth to leave a cavity in the bone underlying the gums;
providing an implant;
surrounding said implant with resorbant material by rolling said implant in a strip of said resorbant material, said strip having a shape adapted to hold said implant in said cavity in a proper position so that said implant may later serve as a mechanical support;
inserting said implant and said resorbant material into said cavity;
suturing the gums to enclose said implant and said resorbant material within the gums;
waiting for said implant to affix to the bone underlying the gums by ossification and for the gums to heal; whereby
said implant upon affixing may serve to mechanically support a dental prosthesis or device.

3. A method as in claim 2 wherein said step of inserting said implant includes
adding or removing said resorbant material to or from said cavity to achieve said proper position of said implant within said cavity.

4. A method of embedding a dental implant including the steps of:
extracting a tooth to leave a cavity in the bone underlying the gums;
providing an implant;
surrounding said implant with resorbant material by cutting blocks of said resorbant material, and suturing said blocks together about said implant, said blocks having a shape adapted to hold said implant in said cavity in a proper position so that said implant may later serve as a mechanical support;
inserting said implant and said resorbant material into said cavity;
suturing the gums to enclose said implant and said resorbant material within the gums;
waiting for said implant to affix to the bone underlying the gums by ossification and for the gums to heal; whereby
said implant upon affixing may serve to mechanically support a dental prosthesis or device.

5. A method as in claim 4 wherein said step of inserting said implant includes
adding or removing said resorbant material to or from said cavity to achieve said proper position of said implant within said cavity.

6. A method of embedding a dental implant including the steps of:
providing an implant;
forming resorbant material into at least one piece adapted to surround said implant and to hold said implant within a cavity in the bone underlying the gums in a proper position so that said implant may later serve as a mechanical support;
surrounding said implant with said piece;
extracting a tooth to leave said cavity;
inserting said implant and said piece into said cavity;
suturing the gums to enclose said implant and said piece within the gums;
waiting for said implant to affix to the bone underlying the gums by ossification and for the gums to heal; whereby
said implant upon afixing may serve to mechanically support a dental prosthesis or device.

7. A method of embedding a dental implant including the steps of:
extracting a tooth to leave a cavity in the bone underlying the gums;
providing an implant;
inserting said implant into said cavity;
packing voids in said cavity with resorbant material to hold said implant in said cavity in a proper position so that said implant may later serve as a mechanical support;
suturing the gums to enclose said implant and said resorbant material within the gums;
waiting for said implant to affix to the bone underlying the gums by ossification and for the gums to heal; whereby
said implant upon affixing may serve to mechanically support a dental prosthesis or device.

* * * * *